United States Patent [19]

Stavinoha, Jr.

[11] Patent Number: 5,756,779
[45] Date of Patent: May 26, 1998

[54] RECOVERY OF 3,4-EPOXY-1-BUTENE FROM 1,3-BUTADIENE OXIDATION EFFLUENTS

[75] Inventor: Jerome Leonard Stavinoha, Jr., Longview, Tex.

[73] Assignee: Eastman Chemical Company, Kingsport, Tenn.

[21] Appl. No.: 939,393

[22] Filed: Sep. 29, 1997

[51] Int. Cl.⁶ .......................... C07D 301/10; C07D 301/32
[52] U.S. Cl. .................... 549/532; 549/533; 549/534; 549/538
[58] Field of Search .................... 549/532, 533, 549/534, 538

[56] References Cited

U.S. PATENT DOCUMENTS

| | | | |
|---|---|---|---|
| 4,897,498 | 1/1990 | Monnier et al. | 549/534 |
| 4,950,773 | 8/1990 | Monnier et al. | 549/534 |
| 5,117,012 | 5/1992 | Stavinoha et al. | 549/538 |
| 5,312,931 | 5/1994 | Stavinoha | 549/538 |

*Primary Examiner*—C. Warren Ivy
*Assistant Examiner*—Lyman H. Smith
*Attorney, Agent, or Firm*—Michael J. Blake; Harry J. Gwinnell

[57] ABSTRACT

Disclosed are improved processes for the recovery of 3,4-epoxy-1-butene (epoxybutene) from an epoxidation effluent comprising epoxybutane, butadiene, oxygen and an inert diluent obtained by the selective epoxidation of butadiene with an oxygen-containing gas in the presence of a catalyst and an inert gas. Epoxybutene is separated from the effluent by means of an absorption process using an extractant comprising liquid butadiene and, optionally, a hydrocarbon diluent. The formation of butenediols, by the reaction of epoxybutene and water, in the recovery process is inhibited by the addition of a base, preferably an alkali metal base, to the recovery system.

5 Claims, 1 Drawing Sheet

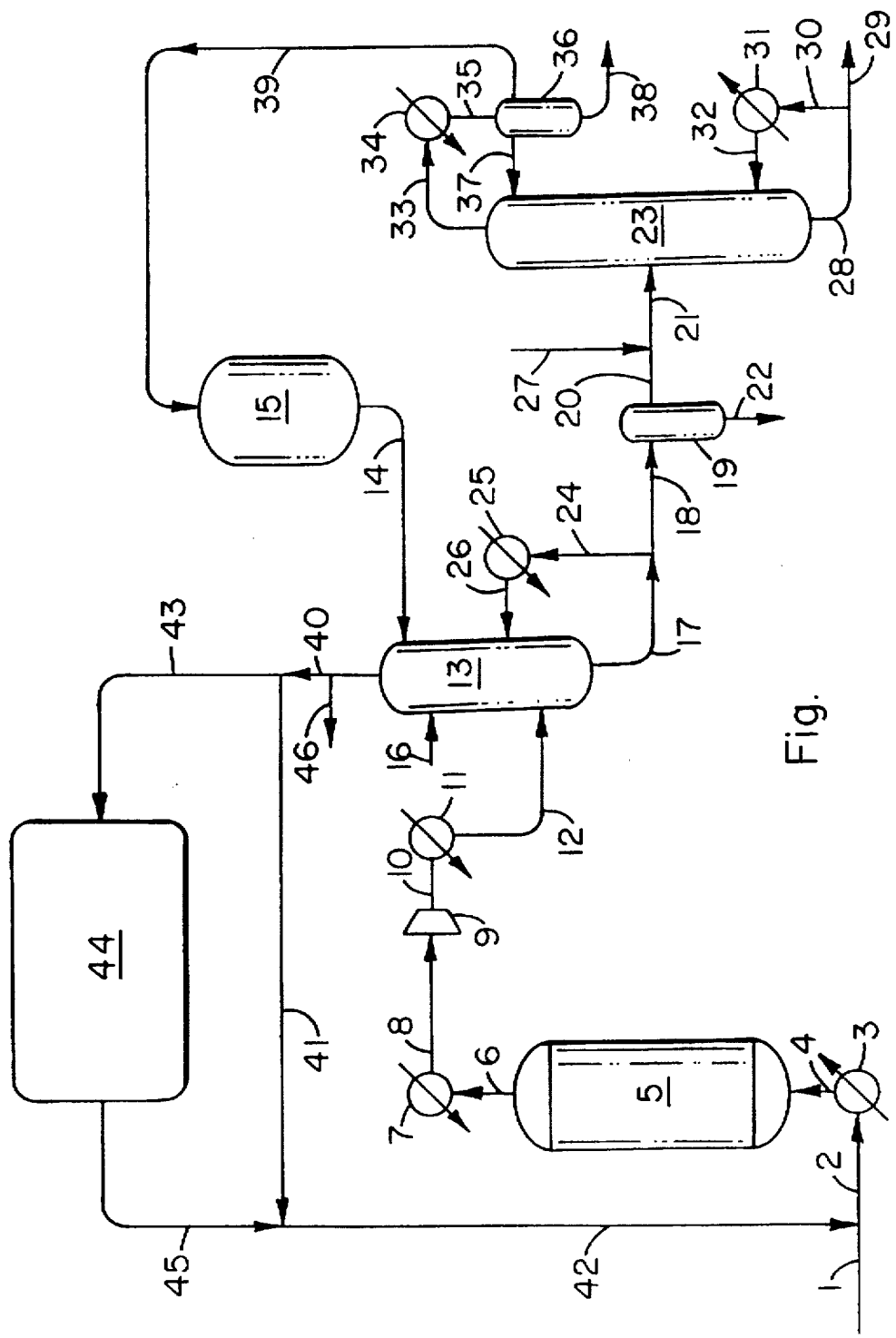
Fig.

RECOVERY OF 3,4-EPOXY-1-BUTENE FROM 1,3-BUTADIENE OXIDATION EFFLUENTS

RECOVERY OF 3,4-EPOXY-1-BUTENE FROM 1,3-BUTADIENE OXIDATION EFFLUENTS

This invention pertains to an improvement in the recovery of 3,4-epoxy-1-butene from an oxidation effluent comprising 3,4-epoxy-1-butene, unreacted 1,3-butadiene, an inert diluent, and oxygen produced by the selective oxidation of 1,3-butadiene. More specifically, this invention pertains to the aforesaid recovery process wherein the formation of diols during the recovery process is inhibited by the addition of a base to the recovery system. The addition of base inhibits the reaction of water present in the system with 3,4-epoxy-1-butene to form butenediols (3-butene-1,2-diol and 2-butene-1,4-diol) and higher oligomers, thereby increasing the yield of 3,4-epoxy-1-butene.

U.S. Pat. Nos. 4,897,498 and 4,950,773 disclose processes for the manufacture of 3,4-epoxy-1-butene (referred to herein as epoxybutene) by the selective epoxidation of 1,3-butadiene (referred to herein as butadiene) wherein butadiene is contacted with an oxygen-containing gas in the presence of certain silver catalysts. To achieve high yields of epoxybutene (based on the butadiene consumed), especially when operating on a commercial scale, it is necessary to maintain the conversion of the butadiene at relatively low levels, e.g., from about 2 to 30 mole percent based on the butadiene fed to the epoxidation zone. The epoxidation effluent thus contains significant amounts of butadiene which must be recovered and recycled to the epoxidation zone. Obtaining a high yield of epoxybutene also requires the presence of an inert gas diluent in the gas feed to the epoxidation zone. An inert gas such as methane, nitrogen, helium, or the like, constituting from about 25 to 85 mole percent of the gas feed to the epoxidation zone, is usually employed.

Epoxybutene is a very reactive compound which can be used to manufacture a variety of chemicals. Due to its reactivity, the recovery of epoxybutene from epoxidation effluents must be performed under mild conditions to avoid the conversion of epoxybutene to other undesired compounds such as butenediols and oligomers. It is possible to recover epoxybutene directly from the epoxidation effluent by compressing the gaseous effluent to pressures sufficiently high to liquefy the epoxybutene. However, the compression of the effluent would require the use of a series of compressors and heat exchangers to remove the heat of compression and maintain the epoxybutene at a temperature which would minimize by-product formation.

The recovery of gaseous products by absorption techniques wherein a gaseous stream is contacted with a liquid absorbent, also referred to as an extractant or solvent, is well known. U.S. Pat. Nos. 5,117,012 and 5,312,931 disclose processes for the recovery of epoxybutene from an oxidation effluent comprising epoxybutene, butadiene, an inert diluent gas, and oxygen by contacting the oxidation effluent with liquid butadiene, or a mixture of liquid butadiene and butane, in an absorption zone to obtain a solution of epoxybutene in either butadiene or a mixture of butane and butadiene. One problem involved in the recovery processes disclosed in U.S. Pat. Nos. 5,117,012 and 5,312,931 is the formation of butenediols (3-butene-1,2-diol and 2-butene-1,4-diol) in the recovery zone. Butenediol formation by the reaction of epoxybutene with water can lower the yield of epoxybutene by up to 5 mole percent. Complete elimination of water from the epoxybutene recovery process is not possible since water is formed in the butadiene oxidation portion of the manufacturing process.

I have discovered that the formation of butenediols (3-butene-1,2-diol and 2-butene-1,4-diol) and higher oligomers can be reduced by adding a base to the absorber utilized in the recovery processes described in U.S. Pat. Nos. 5,117,012 and 5,312,931. It is believed that formic acid formed in the epoxybutene manufacturing process causes or catalyzes the reaction of epoxybutene and water resulting in the formation of butenediols. Neutralization of the formic acid by the addition of base addition according to the present invention inhibits and reduces butenediol formation. The present invention, therefore, pertains to an improved process for the recovery of epoxybutene from a substantially-gaseous effluent from an epoxidation zone wherein butadiene is contacted with an oxygen-containing gas in the presence of a catalyst and an inert diluent, to produce an epoxidation effluent comprising epoxybutene, butadiene, oxygen, an inert diluent and water which comprises feeding the effluent to an absorption vessel wherein the effluent is intimately contacted with an extractant comprising liquid butadiene or a mixture of liquid butane and liquid butadiene at a pressure of about 2 to 10 bars and a temperature of about 0 to 60° C. to obtain:

(1) a vapor effluent comprising the extractant and oxygen from the upper section of the absorption vessel; and
(2) a liquid effluent comprising epoxybutene, the extractant and water from the lower section of the absorption vessel;

wherein a basic compound is fed to the absorption vessel, whereby formation of butenediols (3-butene-1,2-diol and 2-butene-1,4-diol) in the epoxybutene recovery system is reduced. As used herein, the term butane refers to C-4 hydrocarbons in general such as normal butane, isobutane, cyclobutane and mixtures thereof. The butane used in the operation of the epoxybutene production system described herein is comprised of approximately 95% normal butane with minor amounts of other C-4 and C-5 compounds.

The accompanying Figure is a process flow diagram illustrating an epoxybutene production system embodying the principles of the processes of the present invention. While the present invention is susceptible to embodiment in various forms, there is shown in the Figure and hereinafter described in detail preferred embodiments of the invention. However, the present disclosure is to be considered as an exemplification of the invention without limitation to the specific embodiments illustrated. The pressures referred to herein are given in bars absolute.

The present invention may be used in combination with any epoxidation process wherein butadiene is contacted with an oxygen-containing gas in the presence of a catalyst and an inert gas to produce an epoxidation effluent comprising epoxybutene, butadiene, oxygen, an inert diluent and water. The silver-catalyzed, epoxidation processes described in U.S. Pat. Nos. 4,897,498 and 4,950,773 are typical of those which may be employed in the epoxidation zone. The epoxidation zone comprises one or more reactors of any design that allows removal of the heat of reaction in order to prevent an exothermic temperature excursion from occurring. For example, a shell-and-tube design, typically used for ethylene oxide production, may be employed. Other types of reactor designs include multi-staged adiabatic reactors, fluidized bed reactors, moving or transport bed reactors and the like.

The feed to the epoxidation zone comprises butadiene, an oxygen-containing gas and an inert diluent gas in various proportions. Generally, any oxygen ($O_2$) concentration up to the explosive limit can be used. For example, when using nitrogen as the inert gas, the maximum oxygen concentration normally is in the range of about 9 mole percent. Higher oxygen concentration, e.g., up to about 18 mole percent, may be employed using methane as the inert diluent. When using butane as the inert diluent gas, relatively high oxygen concentrations, e.g., up to about 30 mole percent may be employed. The butadiene concentration typically is about 4 to 50 mole percent. The butadiene:oxygen mole ratio in the feed normally is maintained within the range of about 1:5 to 10:1. The inert gas usually constitutes about 25 to 85 mole percent of the total feed to the epoxidation zone. Normally, the feed also include a small amount, e.g., 1 to 40 parts per million (ppm) of a halide source such as 1,2-dichloroethane. Various other organic halides may be used, many of which are described in U.S. Pat. No. 4,950,773. The concentration of the organic halide in the feed more commonly is in the range of 2 to 10 ppm. The feed also may contain minor amounts, e.g., 5 mole percent or greater, of impurities such as up to about 4 mole percent water and up to 2 mole percent carbon dioxide. Some argon may also be present in the feed. The amount of argon is controlled by purging a small amount of the recycle gas. Typically, the amount of argon is maintained at less than 10 percent.

Although the reactor of the epoxidation zone may be operated at pressures ranging from 0.1 to 20 bars, pressures in the range of about 1 to 3 bars normally are used. The epoxidation feed typically is heated to about 175 to 225° C. in a pre-heater prior to entering the epoxidation reactor. The temperature of the epoxidation effluent is maintained at about 180 to 250° C., preferably about 200 to 230° C., by adjusting the temperatures of the reactor coolant, if employed, and/or pre-heater and/or the concentration of oxygen and/or the organic halide in the feed.

The silver catalysts described in U.S. Pat. No. 4,897,498 are examples of the epoxidation catalysts which may be used to convert butadiene to epoxybutene. The catalyst preferably is a supported, cesium-promoted, silver catalyst.

The gaseous epoxidation effluent typically comprises about 0.5 to 6 mole percent epoxybutene, about 4 to 50 mole percent butadiene, about 4 to 25 mole percent oxygen and about 25 to 85 mole percent inert gas. The effluent also contains a total of about 0.5 to 10 mole percent of water, carbon dioxide, acrolein, furan, vinylacetaldehyde, and crotonaldehyde, formed in the epoxidation zone. Unconsumed organic halide also is present in the epoxidation effluent. Typically the overall selectivity to epoxybutene is about 85–95%. As used herein, the percent conversion of butadiene is:

Moles butadiene converted/Moles butadiene fed X 100 and the percent selectivity to 3,4-epoxy-1-butene is:

Moles butadiene converted to 3,4-epoxy-1-butene/Moles butadiene converted X 100

The epoxidation effluent is fed to a cooling/compression zone comprising one or more heat exchangers and one or more compressors wherein the effluent is pressurized to a pressure of about 3 to 10 bars absolute and cooled to a temperature of about 0 to 100° C. The cooling/compression zone may include a gas/liquid separator to remove any condensed liquids, e.g., water and/or butenediols (3-butene-1,2-diol and 2-butene-1,4-diol), from the pressurized and cooled effluent prior to feeding it to the absorption zone. The oxidation effluent which then is fed to the absorption zone contains about 1 to 5 mole percent water and formic acid, typically about 0.5 to 5 ppm (v/v) formic acid.

The absorption zone comprises a columnar, pressure vessel containing trays or a packing material which facilitates intimate gas/liquid contact. Examples of suitable packing material include Koch-Sulzer packing, Pall rings, Berl saddles, and Penn State packing. The absorption vessel normally is provided with means, such as a disengaging space above the packing, to prevent or minimize entrainment of liquids in the gas stream removed from the upper section thereof. The pressurized, cooled, substantially gaseous, epoxidation effluent is fed to the lower section of the absorption vessel, preferably near the bottom of the vessel. Liquid butadiene or a liquid mixture of butane and butadiene is fed to the upper section, preferably near the top, of the absorption vessel and flows downward, thereby absorbing or scrubbing the epoxybutene component from the upwardly-flowing epoxidation effluent. When a mixture of butane and butadiene is used as the absorber solvent, the butane:butadiene mole ratio, normally is maintained in the range of about 20:1 to 1:2 with mole ratios of about 12:1 to 2:1 being preferred. A solution of epoxybutene in butadiene, or a mixture of butane and butadiene, is removed from the base of the absorption vessel and a vapor comprising butadiene, butane or other inert diluent, oxygen and carbon dioxide components of the epoxidation effluent is removed from the top of the vessel.

As stated hereinabove, the epoxidation effluent is intimately contacted with butadiene, or a mixture of liquid butane and butadiene, in the absorption zone at a pressure of about 2 to 15 bars and a temperature of about 0 to 60° C. The absorption zone preferably is operated at pressures and temperatures of about 3 to 13 bars and about 0 to 60° C. to minimize the reaction of the epoxybutene with the minor amounts of active hydrogen compounds present. In a preferred embodiment of my invention, the particular combination of pressure and temperature are selected to provide a predetermined concentration of butadiene, e.g., about 4 to 50, preferably about 7 to 20, mole percent, in the vapor effluent removed from the absorption vessel. The butadiene-containing vapor effluent thus obtained can be recycled, directly or indirectly, to the epoxidation zone and provide all of the butadiene reactant and diluent for the epoxidation reaction. When butane is employed as the inert diluent gas, the ratio of butane to butadiene in the absorber solvent also determines the concentration of these components in the gas effluent from the absorber. Thus, the butane:butadiene mole ratio in the absorber solvent is maintained to provide an absorber gas effluent containing about 4 to 50, preferably about 7 to 20, mole percent of butadiene, and about 25 to 85, preferably about 40 to 80, mole percent of butane. The mole percent composition of the vapor effluent from the absorber may be determined by applying both Dalton's law and Raoult's law to the components of the absorber.

The amount of the liquid butadiene or mixture of butane and butadiene mixture fed to the absorption vessel can vary substantially depending, for example, on the particular vessel, packing material and conditions employed and the feed rate and composition of the epoxidation effluent fed. Generally, the weight ratio of the absorber solvent feed to epoxidation effluent feed is in the range of about 0.1:1 to about 0.6:1. The temperature of the liquid butadiene or liquid mixture of butane and butadiene fed typically is in the range of about 0 to 60° C.

A base compound also is fed to the absorption vessel for the purpose of reducing the formation of butenediols. Generally, any basic material which is capable of neutralizing formic acid may be used in the present process. Examples of suitable bases include the Group 1a (alkali) metal hydroxides, bicarbonates and carbonates; the Group 2a (alkaline earth) metal hydroxides and carbonates, amines such as tertiary amines, e.g., trialkylamines containing up to about 18 carbon atoms, amino alcohols such as tertiary aminoalkanols, e.g., N,N-dialkylaminoalkanols containing up to about 20 carbon atoms, basic ion-exchange resins, and similar materials. Group 1a metal carbonates and bicarbonates, especially the carbonates and bicarbonates of sodium and potassium, are preferred as the basic material. Since water is removed in the absorber, the base may be added as an aqueous solution to the absorber. It is preferred that the base employed not react with or catalyze the reaction of epoxybutene and that the base not be soluble in either butadiene or butane. The basic compound or material may be removed from the absorber liquid effluent by a decanter if the base is water soluble. If the base is an insoluble material, e.g., a basic ion-exchange resin, it may be held in place as a fixed bed or removed by filtration. The base compound may be added separately to the absorption vessel, typically to the upper section thereof, or it may be fed to the absorber underflow recycle line described hereinbelow. It also is possible to add a basic compound at a point upstream from the absorber although such mode of addition is not ordinarily preferred. The preferred alkali metal base compound may be fed as an aqueous solution containing about 0.1 to 30 weight percent, preferably about 0.5 to 10 weight percent, of the alkali metal base compound.

The amount of the alkali metal base compound which is added will vary depending upon the amount of formic acid present in the system. Typically, the weight ratio of the amount of base added to the amount of epoxidation effluent fed to the absorber is about 1:5000 to 1:40,000. Preferably, the amount of base added normally should be only that amount which maintains a pH of about 5 to 9, most preferably a pH of about 6 to 8. Without the addition of base compound to the absorber, the pH of the absorption underflow typically was in the range of about 2 to 3.

A liquid effluent (absorption underflow) comprising a solution of epoxybutene in butadiene, or mixture of butane and butadiene, is removed from the base of the absorption vessel and is fed to a butadiene or butane/butadiene recovery zone. A portion, e.g., up to about 95 volume percent, of the underflow may be recycled to the absorption vessel. The recycle stream optionally may be cooled by means of a heat exchanger and returned to the lower section of the absorption vessel to control or regulate the temperature therein. As mentioned above, the basic compound or material may be added to this recycle stream. The concentration of epoxybutene in the absorption underflow stream may vary substantially, e.g., from about 2 to 40 weight percent based on the total weight of the stream. Normally, the epoxybutene concentration is in the range of about 5 to 15 weight percent (same basis). The underflow also contains minor amounts of water, diol and other materials, e.g., about 1 to 5 weight percent water and from about 0.01 to 2 weight percent diol.

The butadiene (or butane/butadiene) recovery zone comprises a distillation vessel, e.g., a column, a heat source at the base of the vessel, cooling means to condense vapor removed from the top of the vessel and a separator to separate water from the condensed liquid. The absorption column underflow may be fed to the midsection of the recovery column to obtain (1) a gas effluent comprising butadiene or a mixture of butane and butadiene from the upper section of the column and (2) a liquid effluent comprising crude epoxybutene from the lower section of the column. The gas effluent contains a minor amount of water which may be removed from the epoxybutene production system by condensing the effluent to obtain a two-phase, liquid mixture and separating the aqueous phase from the butane/butadiene phase. Water and butadiene or butane form a constant boiling mixture (azeotrope) having a boiling point of approximately 43° C. at 4.8 bars pressure. The water removal may be enhanced by recycling a portion, e.g., up to 95 weight percent, of the condensed butadiene or butane/butadiene phase to the upper section of the butane/butadiene recovery vessel. The water-depleted butadiene or butan/butadiene stream removed from the butane/butadiene recovery zone may be recycled, directly or indirectly, to the absorption zone along with fresh butane/butadiene. Fresh butadiene also must be added to make up for that consumed in the reactor zone. Make-up butadiene and butane may be added with the absorption column underflow to the butane/butadiene recovery zone. However, fresh butane/butadiene may be added at any point in the recycle loop and it is not necessary that the makeup butane/butadiene be added in the liquid mixture of butane and butadiene fed to the recovery column.

The conditions employed within the recovery column may vary significantly depending on the particular apparatus employed. The pressures and temperatures normally are within the range of about 2 to 6 bars and 5 to 150° C. The column preferably is operated at a column base pressure and temperature of about 2.5 to 5 bars and 100 to 130° C. and a column head pressure and temperature of about 2.5 to 5 bars and 5 to 50° C. To prevent the formation of butadiene polymerization products, the butadiene or butane/butadiene recovery preferably is carried out in the presence of a polymerization inhibitor, such as a phenolic compound, e.g., tertiary butyl catechol or an amine oxide compound. The polymerization inhibitor may be added to the upper section of the butane/butadiene recovery column. For example, the formation of butadiene polymerization products is substantially suppressed by the addition of about 100 to 400 ppm of inhibitor, based on the amount of vapor removed from the column, to the top of the recovery column by means of a low-flow addition device such as a syringe pump. The inhibitor also may be added to the base of the absorption vessel and transported to the recovery zone in the liquid effluent stream obtained from the absorption vessel to reduce polymer formation in the transfer lines and tanks.

The liquid underflow obtained from the butadiene or butane/butadiene recovery zone comprises epoxybutene, typically 90 to 99 weight percent epoxybutene, and minor amounts of butane, butadiene, vinyl acetaldehyde, butenediols, vinylcyclohexene, crotonaldehyde and higher boiling impurities. This crude epoxybutene may be further purified by distillation wherein epoxybutene is taken overhead and most of the impurities are removed from the base of the distillation column.

Since the presence of significant amounts of carbon dioxide in the gas fed to the opoxidation zone detrimentally affects the activity of the epoxidation catalyst, the butane/butadiene-containing effluent gas optionally is passed through a carbon dioxide removal zone wherein the carbon dioxide concentration of the gas is reduced to less than about 2 mole percent, preferably less than about 1 mole percent and most preferably to less than about 0.5 mole percent. Carbon dioxide removal may be accomplished by the means described in U.S. Pat. Nos. 5,117,012 and 5,312,931.

Since oxygen is consumed in the epoxidation zone, the oxygen content of the butadiene-containing effluent gas obtained from the epoxybutene absorption zone (or the carbon dioxide removal zone) is supplemented by an oxygen feed prior to feeding the gas to the epoxidation zone. Normally, an organic halide (discussed hereinabove) also is added to the effluent gas.

Referring to the accompanying Figure, a mixture comprising butane, butadiene, oxygen, and an organic halide is fed by conduit 2 to heat exchanger 3 wherein the mixture is preheated to a temperature of about 150 to 225° C. and then is fed via conduit 4 to epoxidation reactor 5. The epoxidation reactor may contain a plurality of steel tubes packed with a silver catalyst such as a cesium-promoted, supported, silver catalyst. The gas feed passes through the catalyst-containing steel tubes wherein butadiene is selectively oxidized to epoxybutene and exits the epoxidation reactor through conduit 6. A heat exchange fluid is passed over the exterior of the reactor tubes to remove the heat of reaction. The temperature and pressure within conduit 6 typically is about 1 to 4 bars and 200 to 240° C.

The epoxidation effluent is fed to heat exchangers 7 and 11 and compressor 9 by conduits 6, 8 and 10 wherein the temperature of the effluent stream is reduced to about 0 to 100° C. and the pressure is increased to about 2 to 12 bars. The cooled and pressurized effluent is transported by conduit 12 to absorber 13.

A mixture of liquid butane and butadiene is fed from butane:butadiene recovery tank 15 through conduit 14 to the upper section of absorber 13 which contains a suitable packing material to provide intimate contact between the effluent fed by line 12 and liquid butane/butadiene mixture fed by line 14. An 0.5 to 10 weight percent aqueous potssium bicarbonate is fed to absorber 13 by line 16. The pressure and temperature within absorber 13 are within the ranges of about 2 to 10 bars and 0°to 60° C., provided that the combination of pressure and temperature maintains a liquid phase within the absorber. The conditions of pressure and temperature also are controlled to provide a predetermined concentration of both butane and butadiene in the gaseous effluent removed from the top of the absorber.

A liquid effluent comprising a solution of epoxybutene in butane/butadiene is removed from the base of absorber 13 and transported via conduits 17 and 18 to water separator 19 and then through conduits 20 and 21 to the mid-section of butane/butadiene recovery column 23. Butadiene or a mixture of butane and butadiene is fed to and combined with conduit 20 through line 27. This stream may contain butadiene to make up for the amount consumed in reactor 5 in addition to the butadiene and butane vented in the purge. The amount of base added to absorber 13 through conduit 16 is sufficient to cause the water removed from separator 19 to have a pH of about 6 to 8. A portion, e.g., up to about 95 weight percent, of the liquid effluent stream may be recycled through conduits 24, heat exchanger 25 and conduit 26 to absorber 13. This recycle stream functions to provide additional cooling of the contents of the absorber.

The concentration of epoxybutene in the liquid solution fed by line 21 to column 23 typically is about 5 to 25 weight percent based on the total weight of the solution. Column 23 typically is equipped with trays or a packing material and is operated at a base pressure and temperature of about 2.5 to 5 bars and 90°to 130° C. and a head (top) temperature of about 2.5 to 5 bars and 5°to 50° C. to vaporize substantially all of the butane/butadiene fed. A liquid stream of crude epoxybutene is removed from column 23 and from the epoxybutene production system via conduits and 29. This stream may be further refined, if necessary, by one or more distillations to increase the purity of the epoxybutene, e.g., up to 99+%.

The heat required to vaporize butadiene or a mixture of butane and butadiene in column 23 is provided by recycling a portion, e.g., up to 95 weight percent, of the liquid stream to column 23 by means of conduit 30, heat exchanger (reboiler) 31 and conduit 32. A vapor comprised of optionally butane, butadiene, and a minor amount of water is removed from column 23 through conduit 33, condensed in heat exchanger 34 and fed by conduit 35 to water separator 36. Water collects in the lower section of separator 36 and is removed from the production system by conduit 38. Separation of the butadiene or the butane and butadiene mixture and water from the other materials fed to column 23 is enhanced by recycling a portion, e.g., from about 50 to 95 weight percent, of the condensed butane or butane/butadiene to the column via line 37. A butadiene polymerization inhibitor also may be added to column 23, for example, by means of line 37. The remainder of the condensed butadiene (or butane/butadiene) is transported by conduit 39 to butadiene (or butane/butadiene) recovery tank 15.

A vapor effluent comprising butadiene, optionally butane, and oxygen is removed from absorber 13 via conduit 40. Normally, the butadiene content of the vapor effluent is within the range of about 4 to 50, preferably about 7 to 20 mole percent. Additionally, butane, if used, usually constitutes about 25 to 85 mole percent of the total feed to the epoxidation zone. The butane- (or butane/butadiene-) containing vapor effluent is conveyed to epoxidation reactor 5 by conduits 41, 42, 2 and 4 and preheater 3 and provides both the butadiene reactant and the inert gas, e.g., butane, for the epoxidation reaction. When using this mode of direct recycle to the epoxidation reactor, a portion of the stream of conduit 40 is purged from the production system through conduit 46 to prevent an excessive accumulation of carbon dioxide in the system. Oxygen is combined via conduit 1 with the effluent of line 42 to bring the concentration of oxygen in the reactor feed to about 5 to 30 mole percent.

Alternatively, all or part of the vapor effluent removed from epoxybutene absorber 13 via line 40 is transported by conduit 43 to carbon dioxide removal zone 44 wherein all or a portion of the carbon dioxide contained in the absorber effluent is removed prior to recycling to epoxidation reactor 5. The apparatus which may be used in the carbon dioxide removal zone is described in U.S. Pat. Nos. 5,117,012 and 5,312,931. A small purge via line 46 is required to remove argon which is an impurity present in the oxygen feed to the epoxidation zone.

The process provided by the present invention is further illustrated by the following example using the epoxybutene production system described in the Figure. The flow rates are given in parts by weight. The epoxidation reactor employed fixed beds of the cesiumpromoted, supported silver catalyst described in U.S. Pat. No. 4,897,498.

A gas mixture comprising butane (inert gas), oxygen, butadiene, water and 4–5 ppm 1,2-dichloroethane is heated to 180° C. in preheater 3 and fed by line 4 to epoxidation reactor 5 at a rate of 24,214 parts per hour at a pressure of 2 to 2.5 bars. An inert gas such as methane is utilized as a means of delivering the 1,2-dichloroethane to the epoxybutene reaction system and normally is not present in a concentration greater than 0.7 weight percent at any point in the process. The epoxidation effluent gas comprising methane, oxygen, butane, butadiene, water, carbon dioxide, epoxybutene and high boilers are removed from reactor 5 via line 6 at the rate of 24,217 parts per hour and transported through heat exchangers 7 and 11 and compressor 9 by lines 6, 8, 10 and 12 to the side and near the bottom of epoxybutene absorber 13 which consists of a 1.8 m section of stainless steel pipe having an inside diameter of approximately 10 cm. The absorber is packed with 14.1 liters of 6.35 mm Penn State packing except for a 0.5 m vacant space at the top. A mixture of liquid butane and butadiene (84.7/15.1 weight percent) is fed at a pressure of 6.5 bars and a temperature of 20° C. by conduit 14 to the side and near the top of absorber 13 at a rate of 6143 parts per hour. A 1 weight percent solution of potassium carbonate is fed via conduit 16 to the side and near the top of absorber 13. The pressure and temperature within the absorber are 4.9 bars and 40° C. A liquid comprising butane, butadiene, epoxybutene, water, butenediols and high boilers is removed from absorber 13 and transported by conduit 17 and 18 to separator 19. Water and butenediols are removed from separator 19 by line 22 at rates of 13 and 5 parts per hour, respectively. The pH of the water×butenediols removed from separator 19 normally is in the range of about 6.6 to 7.5. Make-up butadiene (590 parts) and butane (18 parts) are fed to conduit 20 by means of conduit 27. This make-up material and the remainder of the liquid in the separator is fed through conduit 21 to the mid-section of butane/butadiene recovery column 23 at a rate of 6858 parts per hour. A portion of the conduit 17 stream is removed by line 24, cooled in heat exchanger 25 and recycled via conduit 26 to the lower section of absorber 13 at a rate of 127,220 parts per hour.

Column 23 is operated at a base pressure and temperature of 4.8 bar and 125° C. and a top pressure and temperature of 4.8 bar and 45° C. A liquid stream comprising epoxybutene, butenediols, and high boilers is removed from the base of column 23 and from the production system via conduits 28 and 29 at a rate of 676 parts per hour. A portion of the liquid stream of line 28 is removed by line 30, passed through heat exchanger 31 and fed via line 32 to the lower section of column 23 to maintain a base temperature of 125° C. therein. The crude epoxybuten product of line 29 may be distilled, if necessary, to obtain an overhead epoxybutene product having a purity in excess of 99.5%.

A vapor effluent comprising methane, oxygen, carbon dioxide, butane, and butadiene is removed from absorber 13 through line 40 at a rate of 24,035 parts per hour and is fed by line 43 to carbon dioxide removal zone 44. The vapor effluent may be returned directly to epoxidation reactor 5 via lines 40, 41, 42, 2 and 4 and preheater 3 although the carbon dioxide present in the vapor has been found to adversely affect the epoxidation reaction. A carbon dioxide-depleted vapor effluent is removed from carbon dioxide removal zone 44 and transported to reactor 5 by lines 45, 42, 2 and 4 and preheater 4 at a rate of 23,780 parts per hour. A portion of the line 40 stream is purged (line 46) from the production system at a rate of 24 parts per hour. A mixture of methane, 1,2-dichloroethane and oxygen is combined with the line 42 stream at a rate of 1 part per hour.

In the above example, epoxybutene is produced at a rate of 0.084 Kg per liter catalyst per hour at an average butadiene conversion of 25.5 mole percent and an overall epoxybutene yield of 88.2 percent. This epoxybutene production rate is achieved by operating the described epoxybutene production system continuously for a period of time exceeding 300 hours. Utilizing the principles of the present invention, butenediols (3-butene-1,2-diol and 2-butene-1,4-diol) are produced at a rate of 8–13 g per Kg of 3,4-epoxy-1-butene. When no basic compound is added to absorber 13 through conduit 16, butenediols are produced at a rate of 20 to 65 g per Kg of 3,4-epoxy-1-butene. These butenediol production rates are based on the amounts of butenediols removed from the epoxybutene production system by separator 19 and line 22 and by line 29.

Analyses of the aqueous streams were done with a gas chromatograph (flame ionization detector) using ethylene glycol as an internal standard. Analysis of stream 29 also was made with a gas chromatograph (flame ionization detector) using cyclohexane as an internal standard. Compositions in the gas loop were determined with a gas chromatograph (thermal conductivity detector) using relative response factors. oxygen concentrations in the loop were determined with an Illinois Instruments Model 2555 oxygen analyzer.

The compositions of some of the streams of the preceding example are set forth in Table I wherein the values given are weight percentages based on the total weight of the stream composition. EpB refers to 3,4-epoxy-1-butene and Diols refers to a mixture of 3-butene-1,2-diol and 2-butene-1,4-diol and high boilers include vinyl acetaldehyde, crotonaldehyde and high molecular weight compounds.

TABLE I

| Conduit Stream | $O_2$ | $CO_2$ | $C_4H_6$ | $C_4H_{10}$ | EpB | $H_2O$ | Diols | High Boilers |
|---|---|---|---|---|---|---|---|---|
| 2 | 11.2 | 0.3 | 9.4 | 76.0 | 0 | 0.6 | 0 | 0 |
| 6 | 9.7 | 1.2 | 7.0 | 76.0 | 2.8 | 0.8 | 0 | 0 |
| 12 | 9.7 | 1.2 | 7.0 | 76.0 | 2.8 | 0.8 | 0 | 0 |
| 14 | 0 | 0.1 | 15.1 | 84.7 | 0 | 0 | 0 | 0 |
| 40 | 9.7 | 1.2 | 9.5 | 76.7 | 0 | 0.5 | 0 | 0 |
| 17 | 0.2 | 0.1 | 5.3 | 81.5 | 10.6 | 2.2 | 0.1 | <0.1 |
| 21 | 0.2 | 0.1 | 13.5 | 76.2 | 9.8 | 0.1 | <0.1 | <0.1 |
| 29 | 0 | 0 | 0 | 0 | 99.4 | 0 | 0.3 | 0.3 |
| 22 | 0 | 0 | 0 | 0 | 0 | 96.3 | 3.7 | 0 |

Table II sets forth the results obtained when no base, potassium carbonate or potassium bicarbonate is used in the recovery of epoxybutene produced according to the example presented hereinabove. The values given below "EpB Produced" and "Diol Produced" are the parts by weight of 3,4-epoxy-1-butene and Diol produced per day whereas the values given below "Diol/EpB" are the parts by weight Diol produced per part by weight 3,4-epoxy-1-butene produced.

TABLE II

| Run No. | Base Used | EpB Produced | Diol Produced | Diol/EpB |
|---|---|---|---|---|
| 1 | $KHCO_3$ | 16,120 | 173 | 0.011 |
| 2 | $K_2CO_3$ | 7,590 | 62 | 0.010 |
| 3 | None | 10,850 | 582 | 0.054 |
| 4 | None | 13,750 | 640 | 0.047 |

The invention has been described in detail with particular reference to preferred embodiments thereof, but it will be understood that variations and modifications may be effected within the spirit and scope of the invention.

I claim:

1. Process for the recovery of epoxybutene from a substantially-gaseous, effluent from an epoxidation zone wherein butadiene is contacted with an oxygen-containing gas in the presence of a catalyst and inert diluent to produce an epoxidation effluent comprising epoxybutene, butadiene, oxygen, an inert diluent and water which comprises feeding the effluent to an absorption vessel wherein the effluent is intimately contacted with an extractant comprising liquid butadiene at a pressure of about 2 to 10 bars and a temperature of about 0 to 60° C. to obtain:

(1) a vapor effluent comprising the extractant and oxygen from the upper section of the absorption vessel; and
   (2) a liquid effluent comprising epoxybutene, the extractant and water from the lower section of the absorption vessel;

wherein a basic compound is fed to the absorption vessel, whereby formation of butenediols is reduced; and wherein epoxybutene is 3,4-epoxy-1-butene, butadiene is 1,3-butadiene and butenediols are 3-butene-1,2-diol and 2-butene-1,4-diol.

2. Process according to claim 1 wherein the epoxidation effluent comprises about 0.5 to 6 mole percent epoxybutene, about 4 to 50 mole percent butadiene, about 4 to 25 mole percent oxygen and about 1 to 5 mole percent water and the amount of liquid absorber solvent employed is about 0.1 to 0.6 parts by weight per part by weight epoxidation effluent.

3. Process according to claim 2 wherein the basic compound is selected from the Group 1a metal hydroxides, bicarbonates and carbonates; the Group 2a hydroxides and carbonates, amines, amino alcohols, and basic ionexchange resins.

4. Process according to claim 2 wherein (i) the base compound is selected from the hydroxides, bicarbonates and carbonates of sodium and potassium and is fed as an 0.1 to 30 weight percent aqueous solution and (ii) the amount of base compound fed results in the water phase of effluent (2) from the lower section of the absorption vessel having a pH of about 6 to 8.

5. Process for the recovery of epoxybutene from a substantially-gaseous, effluent from an epoxidation zone wherein butadiene is contacted with an oxygen-containing gas in the presence of a silver catalyst and butane to produce an epoxidation effluent comprising about 0.5 to 6 mole percent epoxybutene, about 4 to 50 mole percent butadiene, about 4 to 25 mole percent oxygen, about 25 to 85 mole percent butane and about 1 to 5 mole percent water which comprises feeding the effluent to an absorption vessel wherein the effluent is intimately contacted with a mixture of liquid butane and butadiene at a pressure of about 3 to 6 bars and a temperature of about 10 to 50° C. to obtain:

(1) a vapor effluent comprising butadiene, butane, and the oxygen from the upper section of the absorption vessel; and (2) a liquid effluent comprising epoxybutene, butane, butadiene and water from the lower section of the absorption vessel; wherein an alkali metal base compound selected from the hydroxides, bicarbonates and carbonates of sodium and potassium is fed to the absorption vessel, whereby formation of butenediols is reduced; and wherein epoxybutene is 3,4-epoxy-1-butene, butadiene is 1,3-butadiene and butenediols are 3-butene-1,2-diol and 2-butene-1,4-diol.

* * * * *